United States Patent
Blanquart et al.

(10) Patent No.: US 11,425,322 B2
(45) Date of Patent: Aug. 23, 2022

(54) COMPREHENSIVE FIXED PATTERN NOISE CANCELLATION

(71) Applicant: DePuy Synthes Products, Inc., Raynham, MA (US)

(72) Inventors: Laurent Blanquart, Westlake Village, CA (US); John Richardson, Westlake Village, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 17/221,972

(22) Filed: Apr. 5, 2021

(65) Prior Publication Data
US 2021/0235031 A1    Jul. 29, 2021

Related U.S. Application Data

(63) Continuation of application No. 16/420,420, filed on May 23, 2019, now Pat. No. 10,972,690, which is a continuation of application No. 14/214,789, filed on Mar. 15, 2014, now Pat. No. 10,341,593.

(60) Provisional application No. 61/790,590, filed on Mar. 15, 2013, provisional application No. 61/790,983, filed on Mar. 15, 2013.

(51) Int. Cl.
| | | |
|---|---|---|
| *A62B 1/04* | (2006.01) | |
| *H04N 5/365* | (2011.01) | |
| *A61B 1/00* | (2006.01) | |
| *G06T 5/00* | (2006.01) | |
| *G06T 5/50* | (2006.01) | |

(52) U.S. Cl.
CPC ......... *H04N 5/365* (2013.01); *A61B 1/00006* (2013.01); *A61B 1/00009* (2013.01); *A61B 1/00057* (2013.01); *G06T 5/002* (2013.01); *G06T 5/50* (2013.01); *G06T 2207/20224* (2013.01)

(58) Field of Classification Search
CPC . A61B 1/005; H04N 2005/2255; H04N 7/188
USPC ................................................... 348/65–70
See application file for complete search history.

(56) References Cited

U.S. PATENT DOCUMENTS

| | | | |
|---|---|---|---|
| 4,011,403 A | | 3/1977 | Epstein et al. |
| 4,433,675 A | | 2/1984 | Konoshima |
| 4,698,515 A | * | 10/1987 | Sepai ............... H04N 5/2173 |
| | | | 348/E5.079 |
| 5,187,572 A | | 2/1993 | Nakamura et al. |
| 5,196,938 A | | 3/1993 | Blessinger |
| 5,241,170 A | | 8/1993 | Field, Jr. et al. |
| 5,748,234 A | | 5/1998 | Lippincott |
| 5,784,099 A | | 7/1998 | Lippincott |
| 6,272,269 B1 | | 8/2001 | Naum |

(Continued)

FOREIGN PATENT DOCUMENTS

EP    1488731 A1    12/2004

OTHER PUBLICATIONS

Fu, X. Understanding the Davinci Preview Engine. Jul. 2008 [retrieved on Jul. 25, 2014] [Retrieved from the internet <URL: http://www.ti.com/lit/an/spraak8a/spraak8a.pdf> entire document.

*Primary Examiner* — Fabio S Lima

(74) *Attorney, Agent, or Firm* — Terrence J. Edwards; TechLaw Ventures, PLLC

(57) ABSTRACT

The disclosure extends to methods, systems, and computer program products for producing an image in light deficient environments having cancelled fixed pattern noise.

20 Claims, 10 Drawing Sheets

(56) References Cited

U.S. PATENT DOCUMENTS

| | | | |
|---|---|---|---|
| 6,331,156 B1 | 12/2001 | Haefele et al. | |
| 6,485,414 B1 | 12/2002 | Neuberger | |
| 6,690,466 B2 | 2/2004 | Miller et al. | |
| 6,692,431 B2 | 2/2004 | Kazakevich | |
| 6,707,485 B1 | 3/2004 | Higuchi et al. | |
| 6,772,181 B1 | 8/2004 | Fu et al. | |
| 6,791,739 B2 | 9/2004 | Ramanujan et al. | |
| 6,800,057 B2 * | 10/2004 | Tsujita | A61B 1/0646 600/109 |
| 6,899,675 B2 | 5/2005 | Cline et al. | |
| 6,900,829 B1 | 5/2005 | Ozawa et al. | |
| 6,921,920 B2 | 7/2005 | Kazakevich | |
| 6,961,461 B2 | 11/2005 | MacKinnon et al. | |
| 6,977,733 B2 | 12/2005 | Denk et al. | |
| 6,982,740 B2 | 1/2006 | Adair et al. | |
| 6,999,118 B2 | 2/2006 | Suzuki | |
| 7,037,259 B2 | 5/2006 | Hakamata et al. | |
| 7,189,226 B2 | 3/2007 | Auld et al. | |
| 7,258,663 B2 | 8/2007 | Doguchi et al. | |
| 7,356,198 B2 | 4/2008 | Chauville et al. | |
| 7,540,645 B2 | 6/2009 | Kazakevich | |
| 7,544,163 B2 | 6/2009 | MacKinnon et al. | |
| 7,545,434 B2 | 6/2009 | Bean et al. | |
| 7,791,009 B2 | 9/2010 | Johnston et al. | |
| 7,792,378 B2 | 9/2010 | Liege et al. | |
| 7,794,394 B2 | 9/2010 | Frangioni | |
| 7,813,538 B2 | 10/2010 | Carroll et al. | |
| 8,040,403 B2 | 10/2011 | Sakamoto et al. | |
| 8,100,826 B2 | 1/2012 | MacKinnon et al. | |
| 8,411,922 B2 | 4/2013 | Lee et al. | |
| 8,559,743 B2 | 10/2013 | Liege et al. | |
| 8,736,007 B2 | 5/2014 | Wu et al. | |
| 9,007,490 B1 * | 4/2015 | Yuan | G06F 3/017 348/241 |
| 10,341,593 B2 | 7/2019 | Blanquart et al. | |
| 10,972,690 B2 | 4/2021 | Blanquart et al. | |
| 2001/0030744 A1 | 10/2001 | Chang | |
| 2002/0024605 A1 * | 2/2002 | Merrill | H04N 5/361 348/E3.018 |
| 2003/0001951 A1 | 1/2003 | Tsujita et al. | |
| 2003/0112473 A1 * | 6/2003 | Robins | H04N 5/361 358/463 |
| 2005/0093991 A1 | 5/2005 | Yokohata et al. | |
| 2005/0234302 A1 | 10/2005 | MacKinnon et al. | |
| 2006/0028442 A1 * | 2/2006 | Bynum | G06F 3/0317 345/157 |
| 2006/0069314 A1 | 3/2006 | Farr | |
| 2006/0249765 A1 * | 11/2006 | Hsieh | H01L 27/14609 257/292 |
| 2008/0031537 A1 * | 2/2008 | Gutkowicz-Krusin | G06T 5/002 382/254 |
| 2008/0045800 A2 | 2/2008 | Farr | |
| 2008/0231725 A1 | 9/2008 | Sakamoto et al. | |
| 2008/0249765 A1 | 10/2008 | Schuijers | |
| 2009/0012361 A1 | 1/2009 | MacKinnon et al. | |
| 2009/0147078 A1 * | 6/2009 | Tani | H04N 5/2354 348/E5.029 |
| 2009/0154809 A1 * | 6/2009 | Fridrich | G06V 10/30 382/181 |
| 2009/0160976 A1 | 6/2009 | Chen et al. | |
| 2009/0225158 A1 * | 9/2009 | Kimoto | A61B 1/000095 382/128 |
| 2009/0268063 A1 | 10/2009 | Ellis-Monaghan et al. | |
| 2009/0292168 A1 | 11/2009 | Farr | |
| 2010/0165087 A1 | 7/2010 | Corso et al. | |
| 2010/0182446 A1 | 7/2010 | Matsubayashi | |
| 2011/0028790 A1 * | 2/2011 | Farr | A61B 1/00142 600/187 |
| 2011/0074943 A1 * | 3/2011 | Modell | A61B 1/000095 348/E7.085 |
| 2011/0181840 A1 | 7/2011 | Cobb | |
| 2011/0237882 A1 | 9/2011 | Saito | |
| 2011/0237884 A1 | 9/2011 | Saito | |
| 2011/0251484 A1 * | 10/2011 | Carpenter | A61B 6/425 600/431 |
| 2011/0298892 A1 * | 12/2011 | Baer | H04N 13/239 348/46 |
| 2012/0004508 A1 | 1/2012 | McDowall et al. | |
| 2012/0035419 A1 * | 2/2012 | Ashida | H04N 5/361 600/109 |
| 2012/0041267 A1 | 2/2012 | Benning et al. | |
| 2012/0078052 A1 | 3/2012 | Cheng | |
| 2012/0162487 A1 * | 6/2012 | Gutkowicz-Krusin | H04N 5/3658 348/241 |
| 2013/0030247 A1 | 1/2013 | Kimoto | |
| 2013/0182934 A1 * | 7/2013 | Topfer | G06V 10/28 382/132 |
| 2019/0281239 A1 | 9/2019 | Blanquart et al. | |

\* cited by examiner

SES pixel offset estimation with small and large w

Modulation of SES index after a gain change

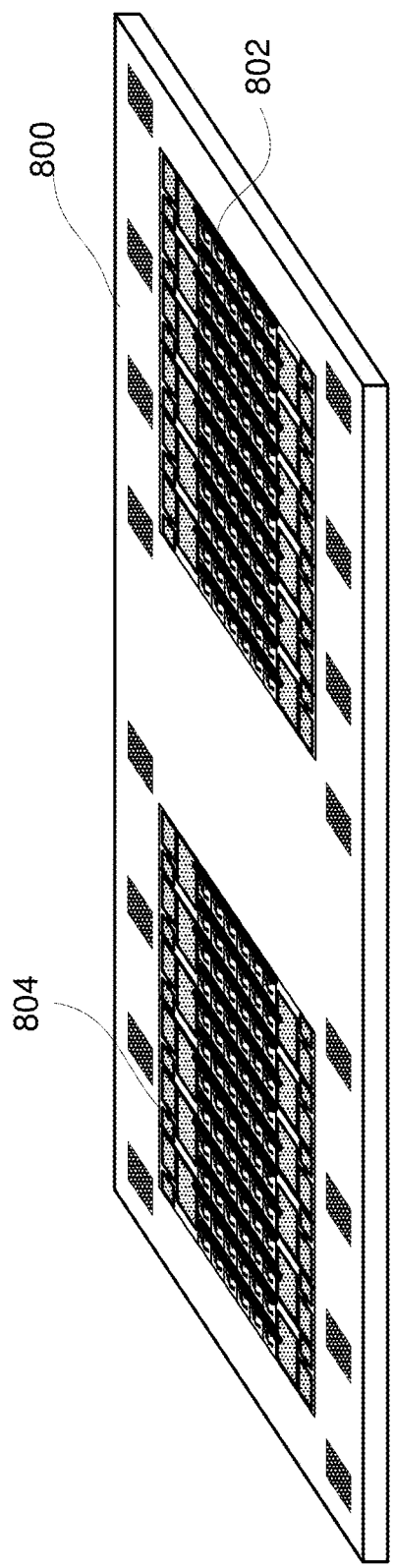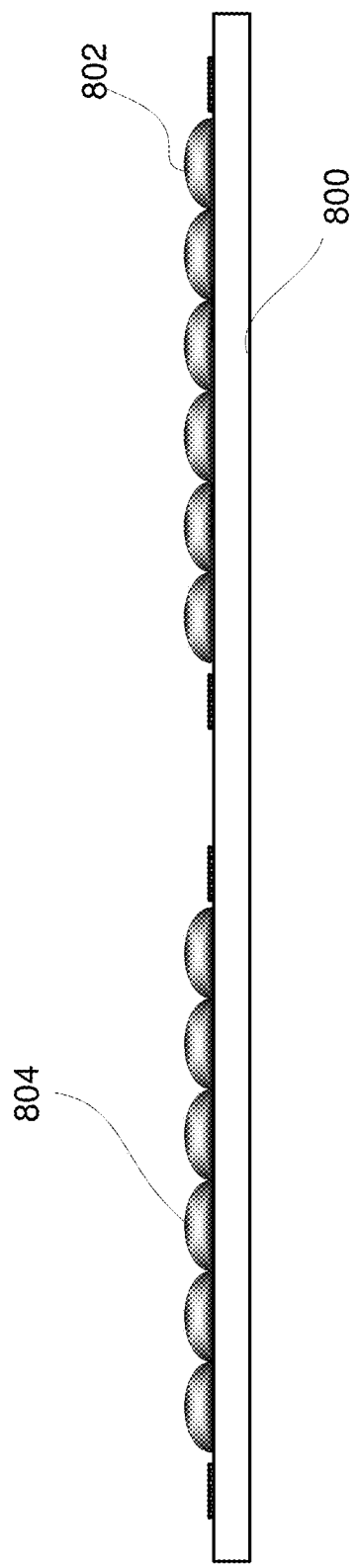
FIG. 8A
FIG. 8B

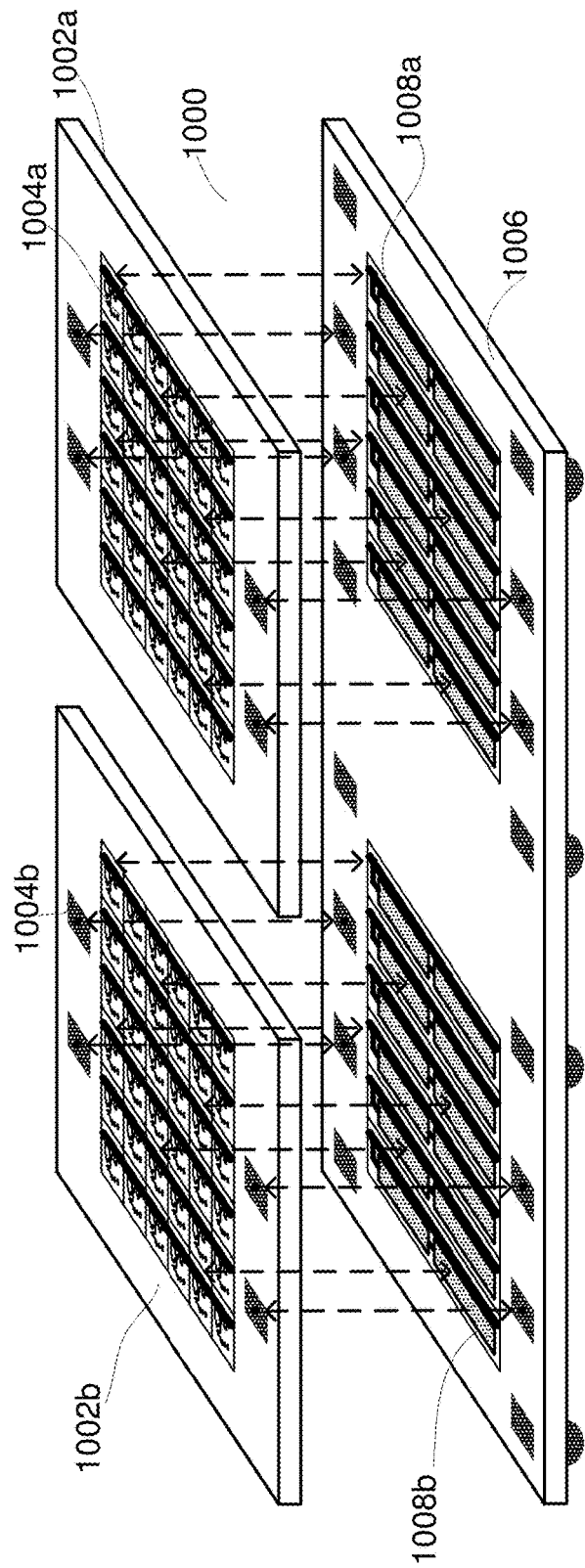
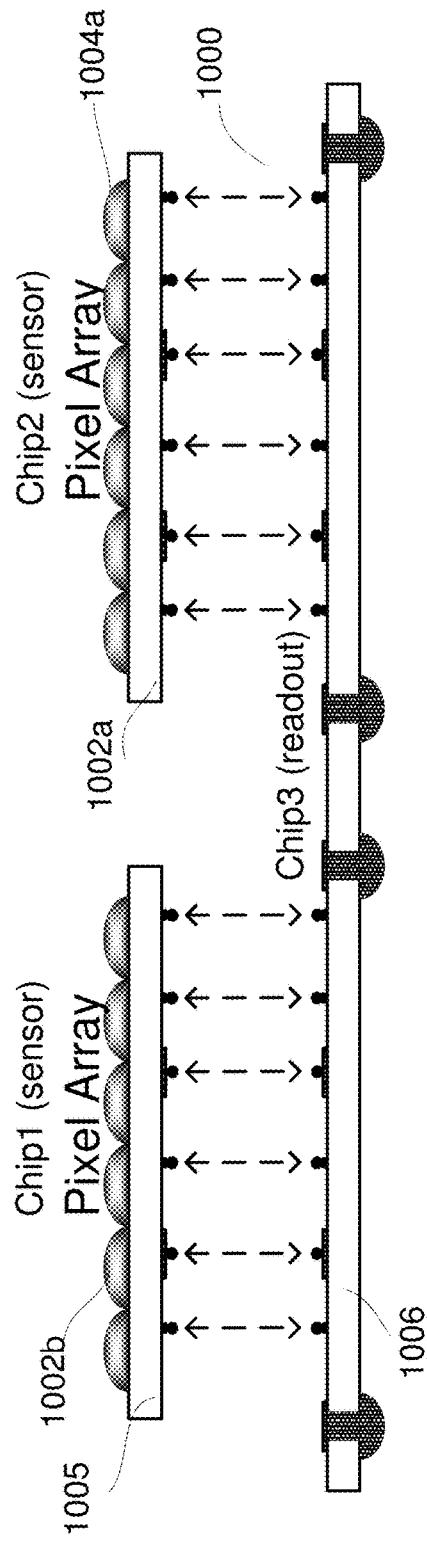
FIG. 10A
FIG. 10B

COMPREHENSIVE FIXED PATTERN NOISE CANCELLATION

CROSS-REFERENCE TO RELATED APPLICATIONS

This application is a continuation of U.S. application Ser. No. 16/420,420, filed May 23, 2019, which is a continuation of U.S. application Ser. No. 14/214,789, filed Mar. 15, 2014 (now U.S. Pat. No. 10,341,593), and which claims the benefit of U.S. Provisional Application No. 61/790,983, filed Mar. 15, 2013, and U.S. Provisional Application No. 61/790,590, filed Mar. 15, 2013, all of which are incorporated herein by reference in their entireties, including but not limited to those portions that specifically appear hereinafter, the incorporation by reference being made with the following exception: In the event that any portion of any of the above-referenced applications is inconsistent with this application, this application supersedes said above-referenced applications.

STATEMENT REGARDING FEDERALLY SPONSORED RESEARCH OR DEVELOPMENT

Not Applicable.

BACKGROUND

Advances in technology have provided advances in imaging capabilities for medical use. One area that has enjoyed some of the most beneficial advances is that of endoscopic surgical procedures because of the advances in the components that make up an endoscope.

The disclosure relates generally to reducing the fixed pattern noise in video streams generated by electromagnetic sensors in order to enhance image quality, to render the data more natural looking in low-light and to improve the color accuracy. The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out in the appended claims.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings.

FIGS. 8A and 8B illustrate a perspective view and a side view, respectively, of an implementation of a monolithic sensor having a plurality of pixel arrays for producing a three dimensional image in accordance with the teachings and principles of the disclosure;

FIGS. 10A and 10B illustrate a perspective view and a side view, respectively, of an implementation of an imaging sensor having a plurality of pixel arrays for producing a three dimensional image, wherein the plurality of pixel arrays and the image sensor are built on a plurality of substrates.

DETAILED DESCRIPTION

The disclosure extends to methods, systems, and computer based products for digital imaging that may be primarily suited to medical applications. In the following description of the disclosure, reference is made to the accompanying drawings, which form a part hereof, and in which is shown by way of illustration specific implementations in which the disclosure may be practiced. It is understood that other implementations may be utilized and structural changes may be made without departing from the scope of the disclosure.

Before the structure, systems and methods for producing an image in light deficient environments having cancelled fixed pattern noise are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

CMOS image sensors have multiple noise sources, the magnitude and appearance of which depend on a range of physical conditions. Pure Poisson or Gaussian temporal noise with no coherent components (e.g. photon shot noise or source follower 1/f read noise) looks as natural as noise can look within a video stream. All other perceivable noise types will degrade the image quality to a much greater extent for the same amplitude. Spatial noise (FPN) is especially egregious and CMOS sensors inherently have at least two sources; pixel FPN and column FPN. The pixel FPN is mostly due to variations in photodiode leakage current (dark signal) from pixel to pixel (DSNU). This source is exponentially dependent on junction temperature ($T_j$) and linearly dependent on exposure time. Column FPN is a consequence of the readout architecture, in which pixels from within the same column are channeled through common analog readout elements.

Figure 1A:
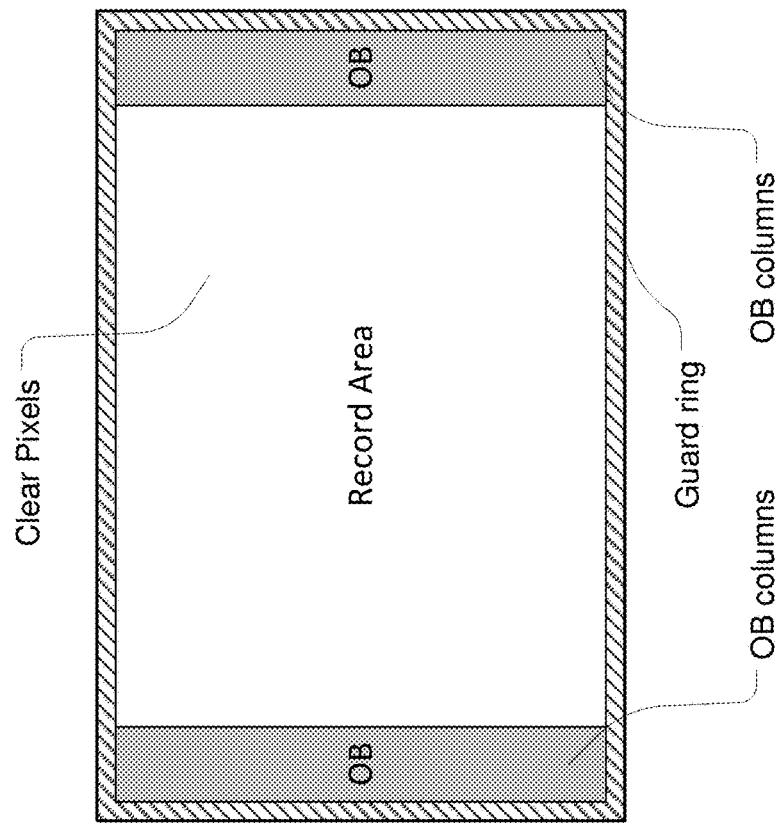
FIG. 1A illustrates a prior art pixel array.

Image sensors usually incorporate special purpose, optically blind, sometimes referred as optical black (OB), rows 110a (at the top and/or bottom of the array) and columns 120a (to the right and/or left of the array), for the purpose of offset calibration. An example layout of a prior art image sensor 100a having clear pixels in a pixel array 130a, a guard ring 140a, with top and bottom OB rows 110a, and left and right OB columns 120a is shown in FIG. 1A. It will be appreciated that the OB rows 110a are usually used to monitor the analog pixel black level, for the OB clamp algorithm. OB rows 110a may also be used by a digital algorithm for the purpose of cancelling column FPN (CFPN). OB columns 120a on the other hand, usually have the purpose of assessing the line offset as a means to cancel out any line-noise. Since line-noise is temporal, the offset may be computed anew for each line in every frame.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the term "proximal" shall refer broadly to the concept of a portion nearest an origin.

As used herein, the term "distal" shall generally refer to the opposite of proximal, and thus to the concept of a portion farther from an origin, or a furthest portion, depending upon the context.

As used herein, color sensors or multi spectrum sensors are those sensors known to have a color filter array (CFA) thereon so as to filter the incoming electromagnetic radiation into its separate components. In the visual range of the electromagnetic spectrum, such a CFA may be built on a Bayer pattern or modification thereon in order to separate green, red and blue spectrum components of the light.

Figure 1B:
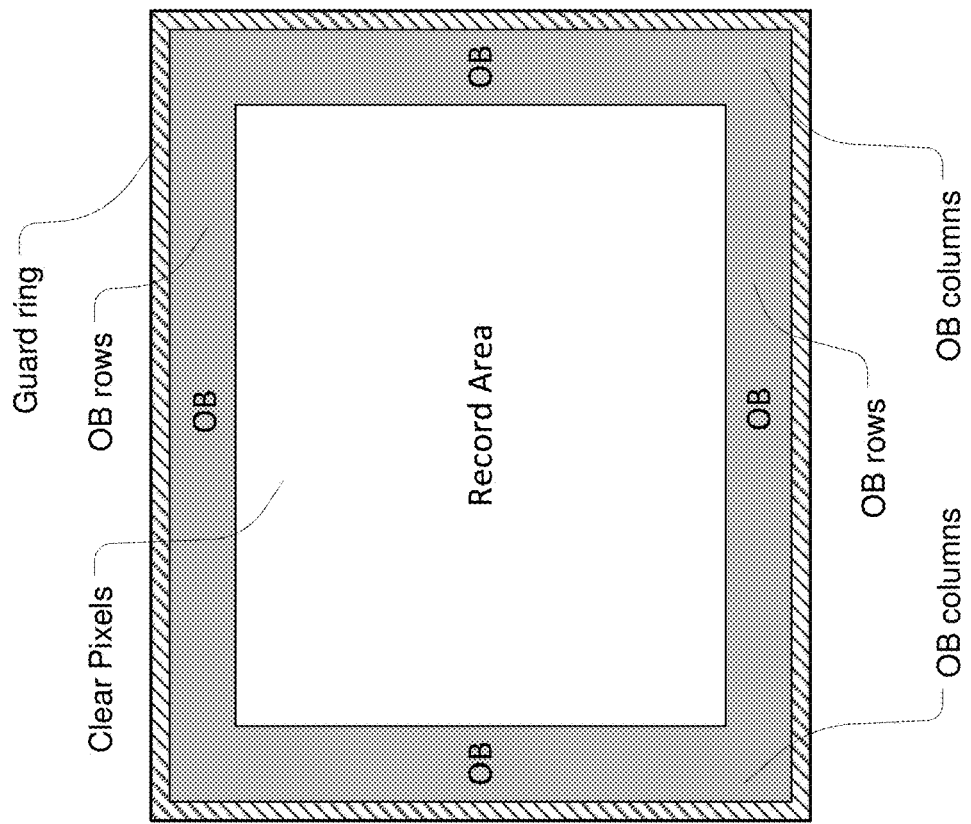
FIG. 1B illustrates a pixel array in accordance with the principles and teachings of the disclosure.

Referring now to FIG. 1B, in a space-constrained environment, it may be desirable to reduce the non-sensitive portion of the sensor 100 as much as possible in order to maximize the area of the light sensing elements, thus preserving image quality. Various measures may be employed to reduce the area of non-light sensing elements in a CMOS sensor, at the level of the sensor and the camera system as a whole. One implementation to reduce the area of non-light sensing elements in a CMOS sensor may be the elimination of the OB rows as described herein, which essentially eliminates an OB-based column fixed pattern noise (CFPN) cancellation method. CFPN cancellation requires black pixel data, with typically 10 to 100 pixels per column, in order to correct for a column-wise random offset prior to reading out the clear pixels 130. Therefore, what is needed is an alternative FPN correction algorithm if OB rows are reduced or eliminated.

It will be appreciated that the disclosure describes systems and methods by which all FPN types, including CFPN, may be cancelled by acquiring frames of dark data, thereby substantially, and perhaps fully, negating the need for a dedicated CFPN correction and its associated OB rows. FIG. 1B illustrates an example of a pixel array 130 in which there are no OB rows present. An off-sensor frame of memory may be used for storing each pixel's calibration data and subsequently cancelling all sources of FPN at the pixel level. Although more memory may be needed for a black frame calibration than for a CFPN algorithm, there may be an advantage in that all sources of FPN (e.g., column FPN, pixel FPN and row FPN) may be eliminated or significantly mitigated.

Figure 2:
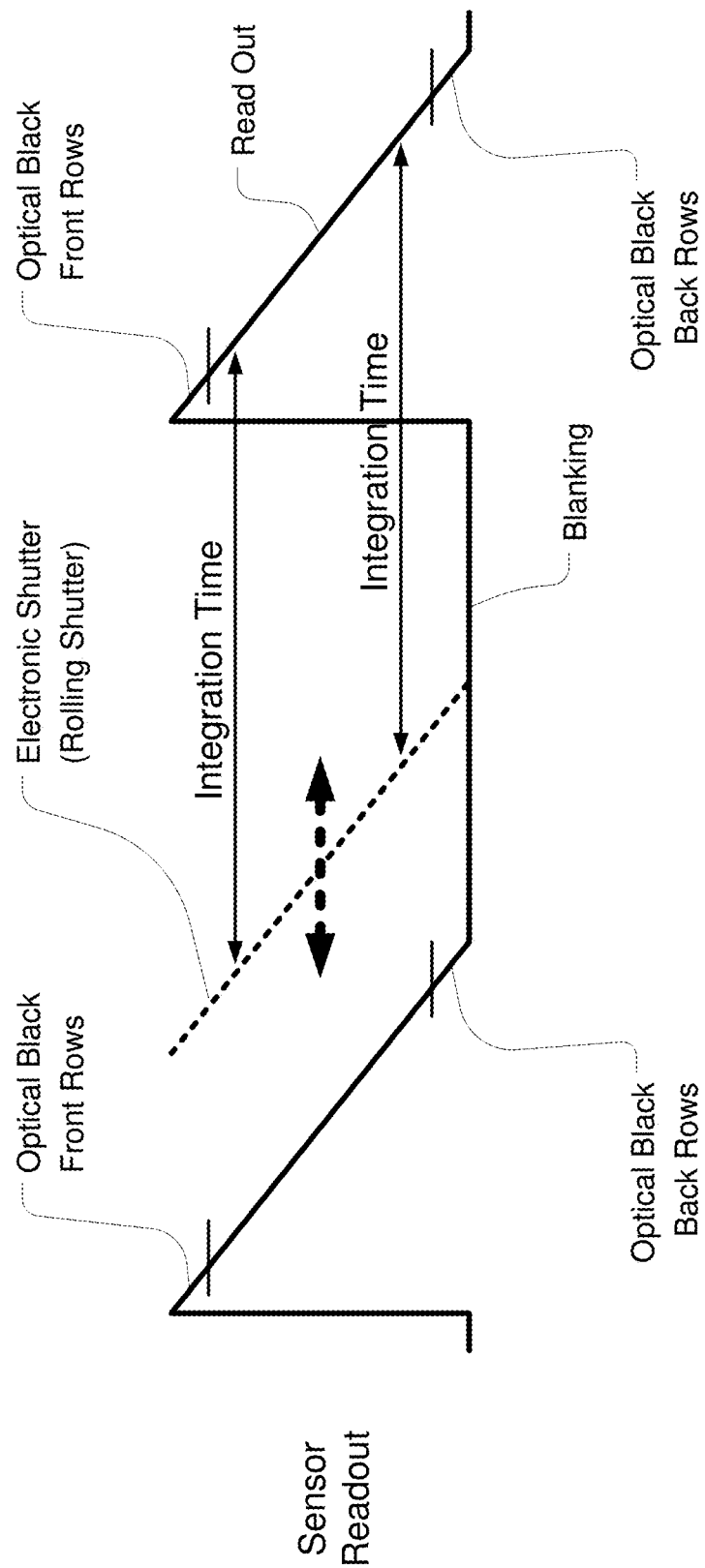
FIG. 2 is an illustration of a graphical representation of image sensor readout operations in accordance with the principles and teachings of the disclosure.

Referring now to FIG. 2, there is illustrated the operational cycles of a sensor used in rolling readout mode or during the sensor readout 200. The frame readout may start at and may be represented by vertical line 210. The read out period is represented by the diagonal or slanted line 202. The sensor may be read out on a row by row basis, the top of the downwards slanted edge being the sensor top row 212 and the bottom of the downwards slanted edge being the sensor bottom row 214. The time between the last row readout and the next readout cycle may be called the blanking time or period 216.

It should be noted that some of the sensor pixel rows might be covered with a light shield (e.g., a metal coating or any other substantially black layer of another material type). These covered pixel rows may be referred to as optical black rows 218 and 220. Optical black columns 218 and 220 may be used as input for correction algorithms. Similar to those illustrated in FIG. 1B, these optical black columns 218 and 220 may be located on the either side of the pixel array. FIG. 2 also illustrates a process of controlling the amount of electromagnetic radiation, e.g., light, that is exposed to a pixel, thereby integrated or accumulated by the pixel. It will be appreciated that photons are elementary particles of electromagnetic radiation. Photons are integrated, absorbed, or accumulated by each pixel and converted into an electrical charge or current. An electronic shutter or rolling shutter (shown by dashed line 222) may be used to start the integration time by resetting the pixel. The light will then integrate until the next readout phase. The position of the electronic shutter 222 can be moved between two readout cycles 202 in order to control the pixel saturation for a given amount of light. It should be noted that this technique allows for a constant integration time between two different lines, but introduces a delay when moving from top to bottom rows. As illustrated in FIG. 2, a sensor may be cycled many times in order to receive data for each pulsed color (e.g., Red, Green, Blue). Each cycle may be timed. In an embodiment, the cycles may be timed to operate within an interval of 16.67 ms. In another embodiment, the cycles may be timed to operate within an interval of 8.3 ms. It will be appreciated that other timing intervals are contemplated by the disclosure and are intended to fall within the scope of this disclosure.

The dark current temperature dependence can be overcome by using a running-average calibration as described herein. In a rolling shutter operation, the pixel integration time may be changed on a frame to frame basis in order to accommodate for the light environment changes (controlled by the auto-exposure algorithm). FIG. 2 illustrates an electronic shutter being adjusted within the frame and therefore controlling the integration time. Because the calibration may be performed at a given integration time, the dark frame correction algorithm may lose efficacy and become inaccurate when trying to correct frames with different integration times. It will be appreciated that each pixel offset has a linear dependence with integration time. One implementation of the disclosure to overcome this issue is to introduce a second calibration point per pixel (which may require a second frame of memory), collected at a different integration time. The pixel calibration data at a given integration time can then be computed using a linear interpolation. However, this technique can introduce interpolation error and complicate significantly the back-end data processing.

Figure 3:
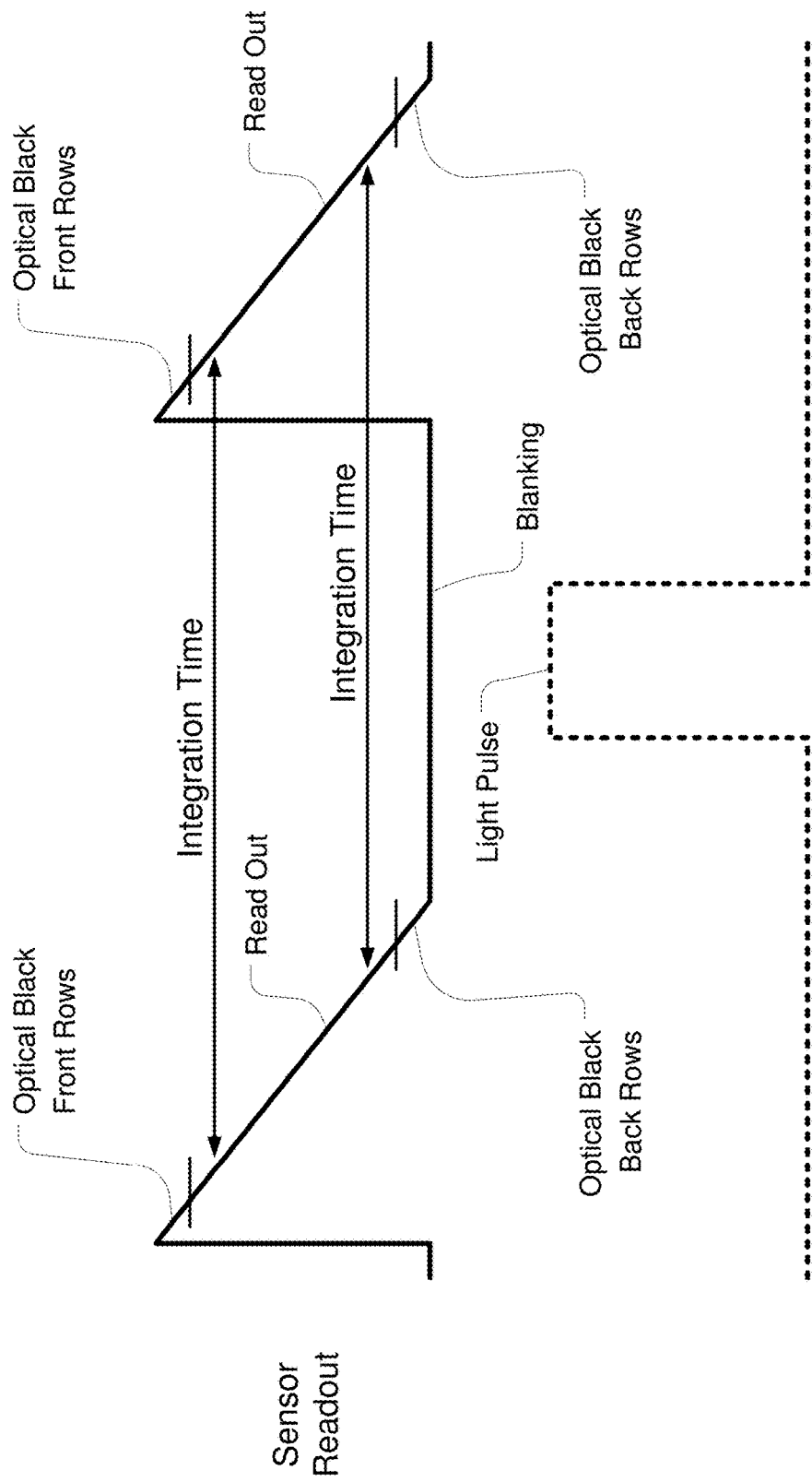
FIG. 3 is an illustration of a graphical representation of image sensor readout operations in accordance with the principles and teachings of the disclosure.

With light pulsing in a light deficient environment, the pixel integration time may be substantially constant from frame to frame. This scenario is illustrated in FIG. 3, where light intensity is adjusted changing the light pulse width or level. As such only one integration time calibration may be required and no interpolation may be needed. As described later, a simple exponential smoothing (SES) method can be used. In such a case, the calibration hardware may comprise only one frame of memory, each memory node containing only one value.

The purpose of the dark frame subtraction process is to adjust for the average offset of each pixel, thus suppressing all FPN types. Since the pixel offsets have temperature dependence, an advantageous scenario would be to have this be a running average process, e.g., by taking sample dark frames at regular intervals and updating the stored correction data.

The resultant quality of this correction may depend on the sampling statistics. In order to predict the resultant effectiveness, the target performance criteria must also be understood.

The uncertainty of a pixel offset estimate is equal to the temporal noise of that pixel divided by the square root of the number of samples. This uncertainty directly translates to post-correction pixel FPN and it is independent of the original FPN. In studies on pixel FPN perception it has been established that at 60 frames per second, the pixel FPN must be less than ¼ of the pixel temporal noise to be unnoticeable. The hardest case is in darkness since that is when the temporal noise is lowest. Since both the perception criterion and the performance depend only on the pixel temporal noise, the estimate of the required statistics is independent of any physical variable:

$$PFPN_{required} \leq \frac{\sigma_T}{4}$$

$$PFPN_{realized} = \frac{\sigma_T}{\sqrt{N_f}}$$

$$\therefore N_f \geq 16$$

where $\sigma_T$ is the pixel temporal noise. Therefore the frame correction process should be effective so long as there are at least 16 dark frames used to compute the average.

Rather than just averaging the most recent, fixed sample of frames, which would require at least 16 frame buffers, a more convenient and efficient method is afforded by simple exponential smoothing (SES). In this case, a single frame buffer would be incrementally adjusted each time a sample dark frame is made available. Each pixel sample taken in the dark is divided by an appropriate binary number ($2^w$) before being added to the buffer content multiplied by $(2^w-1)/2^w$.

Figure 4:
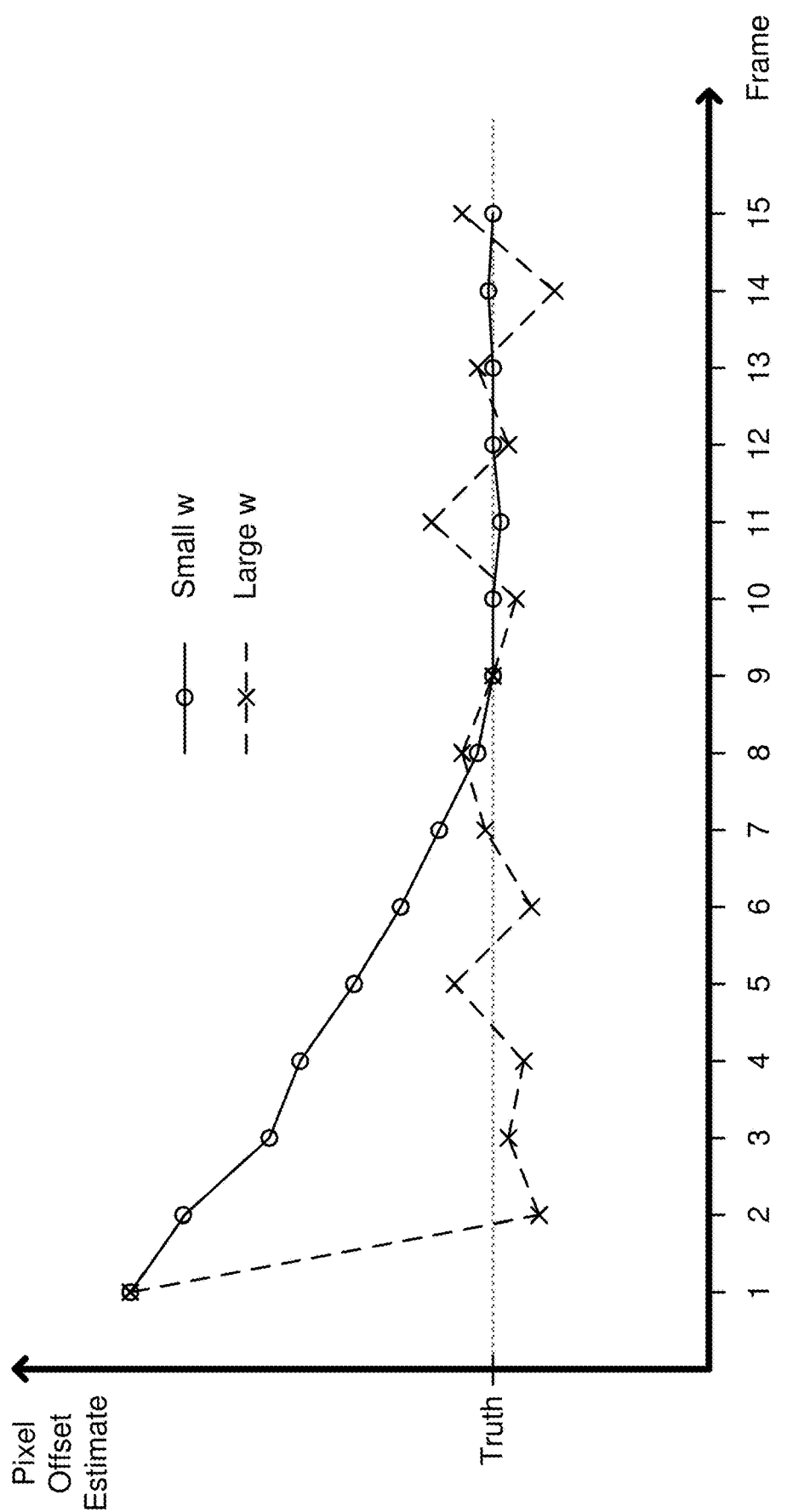
FIG. 4 is a graphical representation of image enhancement in accordance with the principles and teachings of the disclosure.
Figure 5:
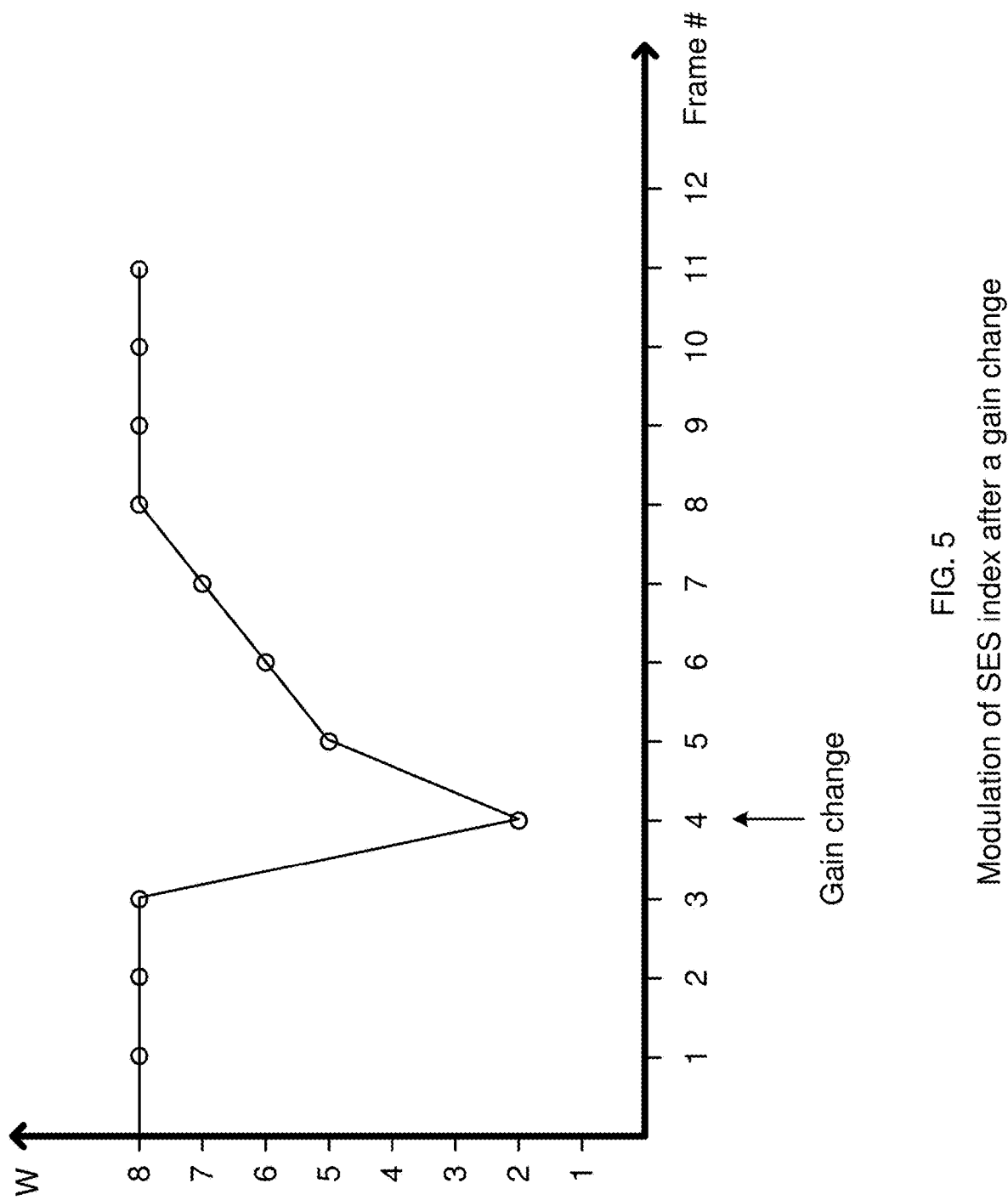
FIG. 5 is a graphical representation of image enhancement in accordance with the principles and teachings of the disclosure.

High values of w, result in greater statistical precision over time in a stable scenario. Lower values of \w will make the correction more reactive to rapid changes, at the expense of precision/stability. See FIG. 4, which illustrates an SES pixel offset estimation with small and large w. Ideally, the values of w would be tunable via control registers. It could be automatically adjusted too, in order to make the correction more reactive at e.g. startup, when $T_J$ is changing the most, or in certain embodiments, following changes in exposure time (if applicable). For example, if a large change in gain or exposure time occurs, it can be lowered and then restored to its baseline incrementally from frame to frame. The increments themselves could vary linearly, e.g., or in a roughly exponential manner as shown in FIG. 5, which illustrates modulation of SES index after a gain change.

SES Capture; on dark frames only:

$$b_{i,j} = d_{i,j} \quad (j = 0)$$

$$b_{i,j} = \frac{1}{2^w} d_{i,j} + \frac{(2^w-1)}{2^w} b_{i,(j-1)} \quad (j > 0)$$

where $b_{i,j}$ is the dark frame correction buffer content for pixel i, following dark frame number j and $d_{i,j}$ is the raw dark data for pixel i, taken from dark frame j. w is a tunable integer.

Application; on non-dark frames only:

$$x'_i = x_i - b_i + B$$

where $x_i$ is the raw data input for pixel i in any non-dark frame and $b_i$ is the current dark frame buffer content. $x'_i$ is the output and B is the black clamp target level.

Figure 6:
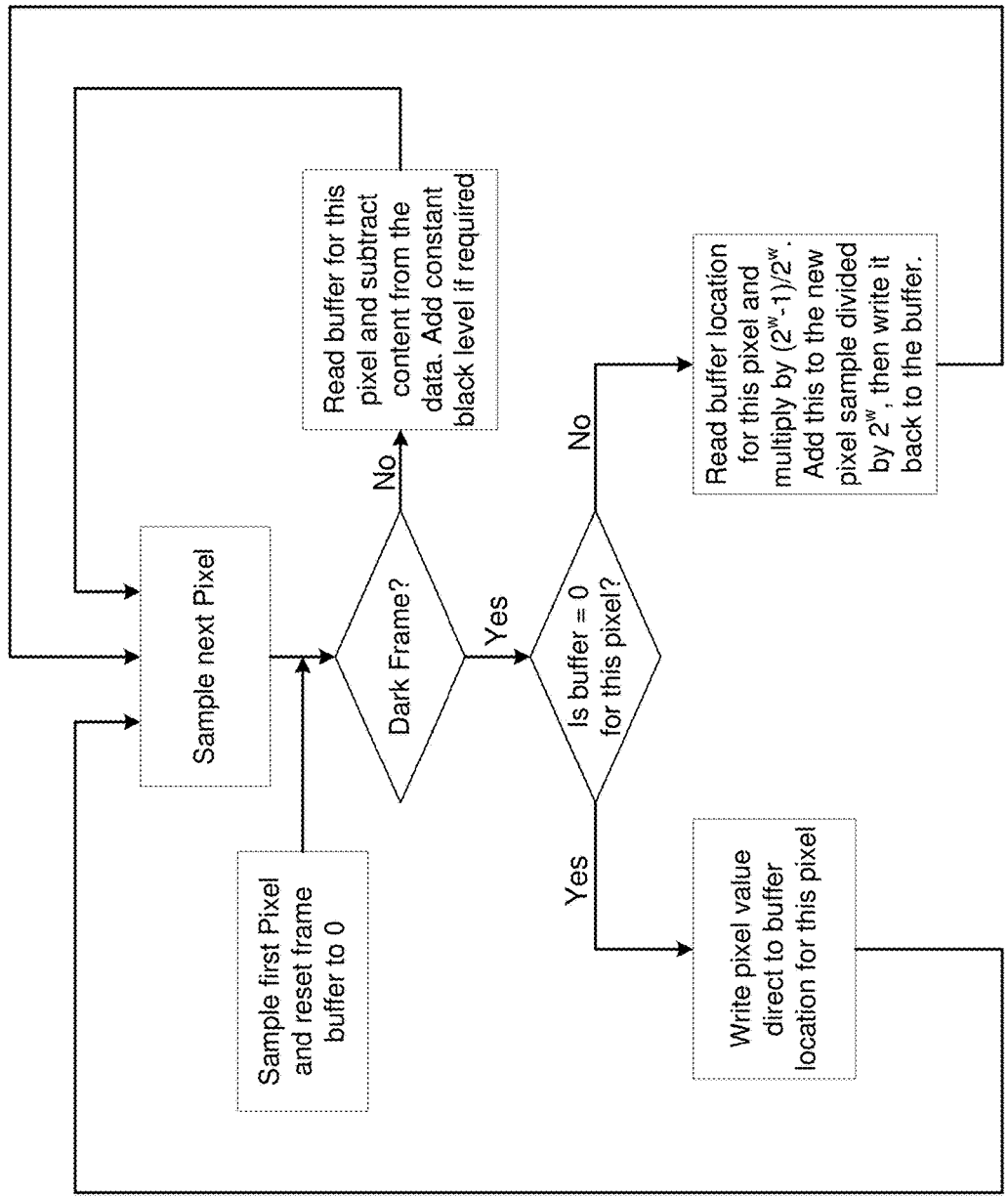
FIG. 6 illustrates a flow chart of image enhancement in accordance with the principles and teachings of the disclosure.

The flowchart in FIG. 6 depicts the overall system, process and method 600. At 610, the system and method 600 may include sampling the first pixel and reset frame buffer to 0. The system and method 600 may determine at 620 whether the sample is a dark frame. If it is determined at 620 that it is a dark frame, then at 630 it is determined whether the buffer for this pixel is 0. If it is determined at 630 that the buffer is 0, then at 640 the pixel value is written directly to the buffer location for this pixel and the next pixel is sampled at 650. If it is determined at 630 that the buffer is not 0, then at 635 read buffer location for this pixel and multiply by $(2^w-1)/2^w$. The result is added to the new pixel sample and divided by $2^w$, then is written to back to the buffer and the next pixel is sampled at 650.

Conversely, if it is determined at 620 that the sample is not a dark frame, then at 625 read buffer for this pixel and subtract content from the data. The method at 625 may also include adding constant black level if required and the next pixel is sampled at 650. Implementations of the disclosure may comprise or utilize a special purpose or general-purpose computer including computer hardware, such as, for example, one or more processors and system memory, as discussed in greater detail below. Implementations within the scope of the disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. In an implementation, a sensor and camera control unit may be networked in order to communicate with each other, and other components, connected over the network to which they are connected. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Figure 7:
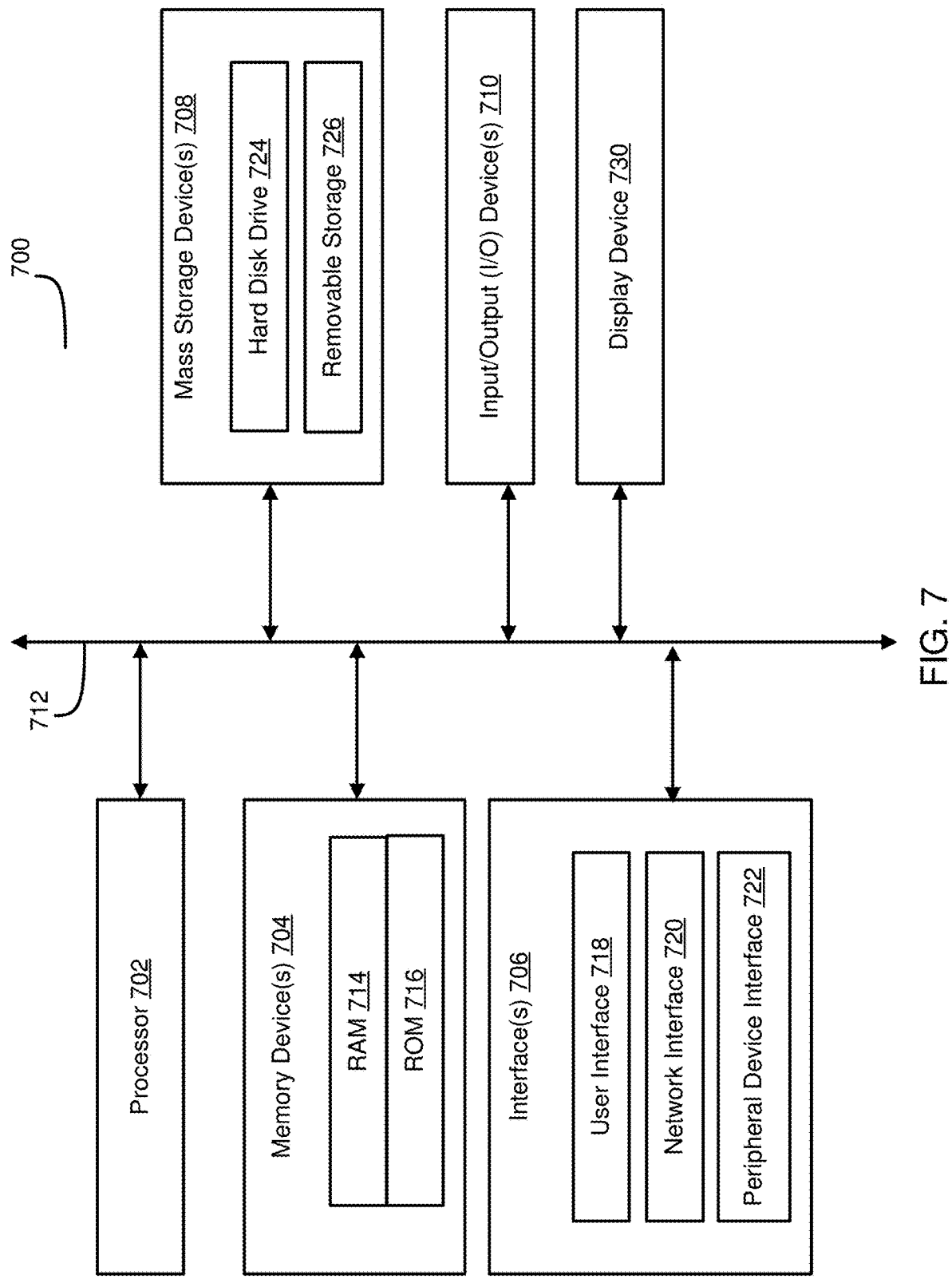
FIG. 7 illustrates a schematic of supporting and enabling hardware in accordance with the principles and teachings of the disclosure.

As can be seen in FIG. 7, various computer system components, program code means in the form of computer-executable instructions or data structures that can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. RAM can also include solid state drives (SSDs or PCIx based real time memory tiered Storage, such as FusionIO). Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, control units, camera control units, hand-held devices, hand pieces, multi-processor systems, microprocessor-based or programmable consumer electronics, network PCs, minicomputers, mainframe computers, mobile telephones, PDAs, tablets, pagers, routers, switches, various storage devices, and the like. It should be noted that any of the above mentioned computing devices may be provided by or located within a brick and mortar location. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) or field programmable gate arrays can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

FIG. 7 is a block diagram illustrating an example computing device 700. Computing device 700 may be used to perform various procedures, such as those discussed herein. Computing device 700 can function as a server, a client, or any other computing entity. Computing device can perform various monitoring functions as discussed herein, and can execute one or more application programs, such as the application programs described herein. Computing device 700 can be any of a wide variety of computing devices, such as a desktop computer, a notebook computer, a server computer, a handheld computer, camera control unit, tablet computer and the like.

Computing device 700 includes one or more processor(s) 702, one or more memory device(s) 704, one or more interface(s) 706, one or more mass storage device(s) 708, one or more Input/Output (I/O) device(s) 710, and a display device 730 all of which are coupled to a bus 712. Processor(s) 702 include one or more processors or controllers that execute instructions stored in memory device(s) 704 and/or mass storage device(s) 708. Processor(s) 702 may also include various types of computer-readable media, such as cache memory.

Memory device(s) 704 include various computer-readable media, such as volatile memory (e.g., random access memory (RAM) 714) and/or nonvolatile memory (e.g., read-only memory (ROM) 716). Memory device(s) 704 may also include rewritable ROM, such as Flash memory.

Mass storage device(s) 708 include various computer readable media, such as magnetic tapes, magnetic disks, optical disks, solid-state memory (e.g., Flash memory), and so forth. As shown in FIG. 7, a particular mass storage device is a hard disk drive 724. Various drives may also be included in mass storage device(s) 708 to enable reading from and/or writing to the various computer readable media. Mass storage device(s) 708 include removable media 726 and/or non-removable media.

I/O device(s) 710 include various devices that allow data and/or other information to be input to or retrieved from computing device 700. Example I/O device(s) 710 include digital imaging devices, electromagnetic sensors and emitters, cursor control devices, keyboards, keypads, microphones, monitors or other display devices, speakers, printers, network interface cards, modems, lenses, CCDs or other image capture devices, and the like.

Display device 730 includes any type of device capable of displaying information to one or more users of computing device 700. Examples of display device 730 include a monitor, display terminal, video projection device, and the like.

Interface(s) 706 include various interfaces that allow computing device 700 to interact with other systems, devices, or computing environments. Example interface(s) 706 may include any number of different network interfaces 720, such as interfaces to local area networks (LANs), wide area networks (WANs), wireless networks, and the Internet. Other interface(s) include user interface 718 and peripheral device interface 722. The interface(s) 706 may also include one or more user interface elements 718. The interface(s) 706 may also include one or more peripheral interfaces such as interfaces for printers, pointing devices (mice, track pad, etc.), keyboards, and the like.

Bus 712 allows processor(s) 702, memory device(s) 704, interface(s) 706, mass storage device(s) 708, and I/O device(s) 710 to communicate with one another, as well as other devices or components coupled to bus 712. Bus 712 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 700, and are executed by processor(s) 702. Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

It will be appreciated that the disclosure may be used with any image sensor, whether a CMOS image sensor or CCD image sensor, without departing from the scope of the disclosure. Further, the image sensor may be located in any location within the overall system, including, but not limited to, the tip of the endoscope, the hand piece of the imaging device or camera, the control unit, or any other location within the system without departing from the scope of the disclosure.

Implementations of an image sensor that may be utilized by the disclosure include, but are not limited to, the following, which are merely examples of various types of sensors that may be utilized by the disclosure.

Referring now to FIGS. 8A and 8B, the figures illustrate a perspective view and a side view, respectively, of an implementation of a monolithic sensor 800 having a plurality of pixel arrays for producing a three dimensional image in accordance with the teachings and principles of the disclosure. Such an implementation may be desirable for three dimensional image capture, wherein the two pixel arrays 802 and 804 may be offset during use. In another implementation, a first pixel array 802 and a second pixel array 804 may be dedicated to receiving a predetermined range of wave lengths of electromagnetic radiation, wherein the first pixel array 802 is dedicated to a different range of wave length electromagnetic radiation than the second pixel array 804.

Figure 9A:
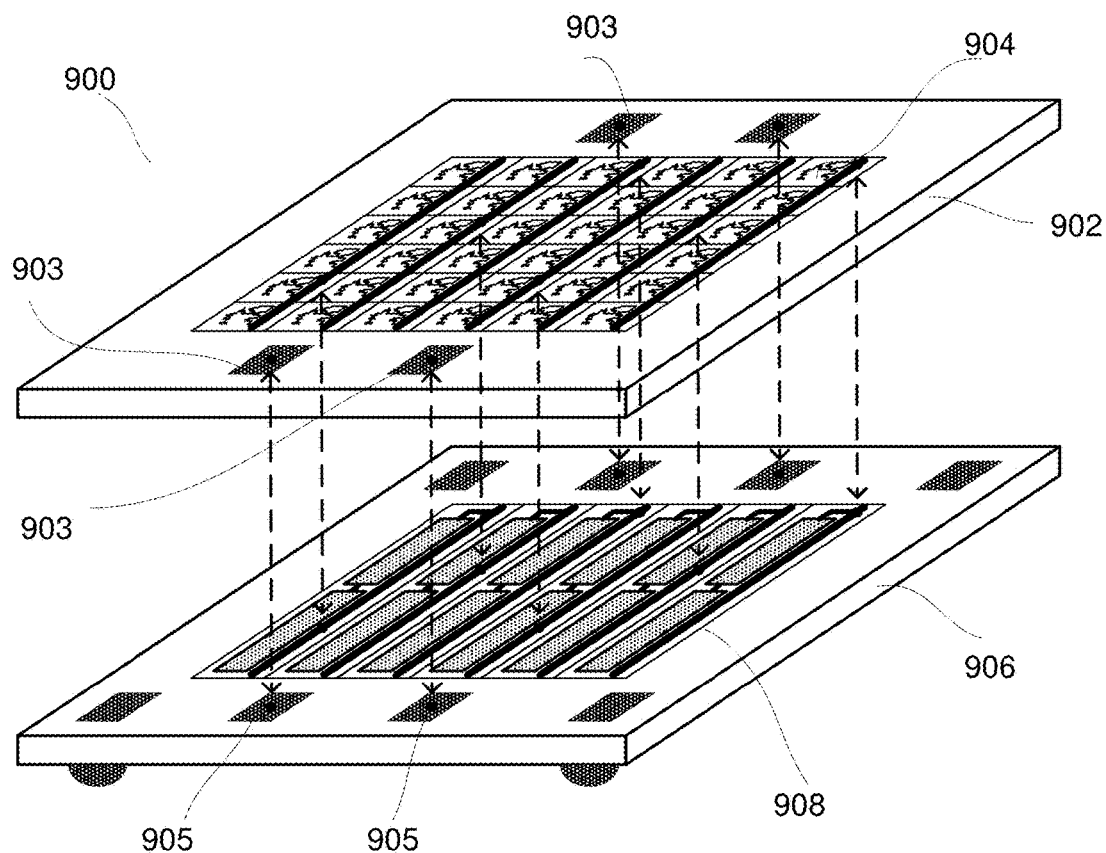
FIGS. 9A and 9B illustrate a perspective view and a side view, respectively, of an implementation of an imaging sensor built on a plurality of substrates, wherein a plurality of pixel columns forming the pixel array are located on the first substrate and a plurality of circuit columns are located on a second substrate and showing an electrical connection and communication between one column of pixels to its associated or corresponding column of circuitry.
Figure 9B:
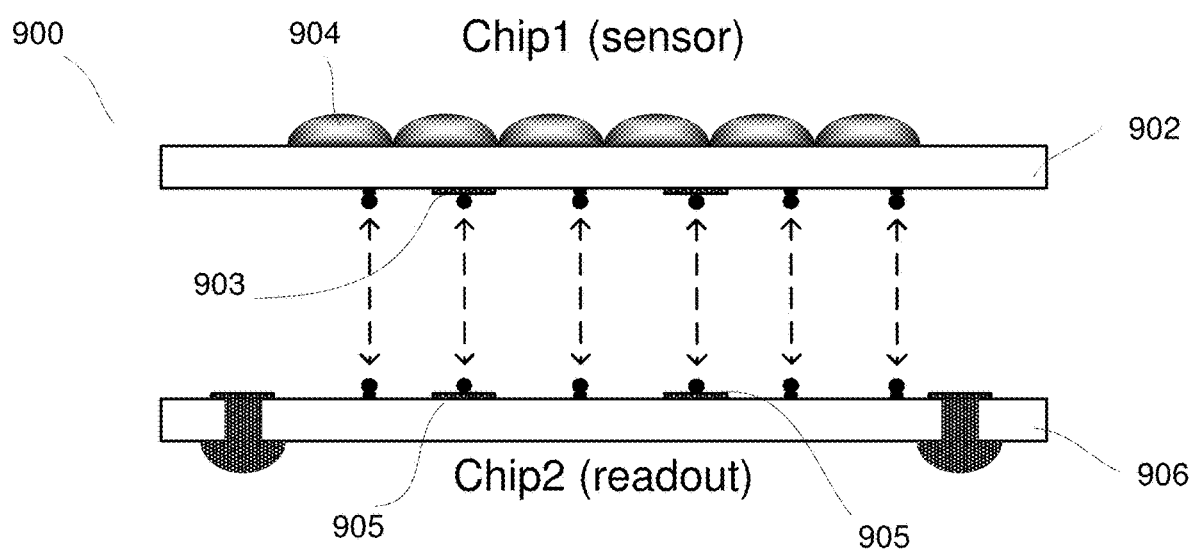

FIGS. 9A and 9B illustrate a perspective view and a side view, respectively, of an implementation of an imaging sensor 900 built on a plurality of substrates. As illustrated, a plurality of pixel columns 904 forming the pixel array are located on the first substrate 902 and a plurality of circuit columns 908 are located on a second substrate 906. Also illustrated in the figure are the electrical connection and communication between one column of pixels to its associated or corresponding column of circuitry. In one implementation, an image sensor, which might otherwise be manufactured with its pixel array and supporting circuitry on a single, monolithic substrate/chip, may have the pixel array separated from all or a majority of the supporting circuitry. The disclosure may use at least two substrates/chips, which will be stacked together using three-dimensional stacking technology. The first 902 of the two substrates/chips may be processed using an image CMOS process. The first substrate/chip 902 may be comprised either of a pixel array exclusively or a pixel array surrounded by limited circuitry. The second or subsequent substrate/chip 906 may be processed using any process, and does not have to be from an image CMOS process. The second substrate/chip 906 may be, but is not limited to, a highly dense digital process in order to integrate a variety and number of functions in a very limited space or area on the substrate/chip, or a mixed-mode or analog process in order to integrate for example precise analog functions, or a RF process in order to implement wireless capability, or MEMS (Micro-Electro-Mechanical Systems) in order to integrate MEMS devices. The image CMOS substrate/chip 902 may be stacked with the second or subsequent substrate/chip 906 using any three-dimensional technique. The second substrate/chip 906 may support most, or a majority, of the circuitry that would have otherwise been implemented in the first image CMOS chip 902 (if implemented on a monolithic substrate/chip) as peripheral circuits and therefore have increased the overall system area while keeping the pixel array size constant and optimized to the fullest extent possible. The electrical connection between the two substrates/chips may be done through interconnects 903 and 905, which may be wirebonds, bump and/or TSV (Through Silicon Via).

FIGS. 10A and 10B illustrate a perspective view and a side view, respectively, of an implementation of an imaging sensor 1000 having a plurality of pixel arrays for producing a three dimensional image. The three dimensional image sensor may be built on a plurality of substrates and may comprise the plurality of pixel arrays and other associated circuitry, wherein a plurality of pixel columns 1004a forming the first pixel array and a plurality of pixel columns 1004b forming a second pixel array are located on respective substrates 1002a and 1002b, respectively, and a plurality of circuit columns 1008a and 1008b are located on a separate substrate 1006. Also illustrated are the electrical connections and communications between columns of pixels to associated or corresponding column of circuitry.

It will be appreciated that the teachings and principles of the disclosure may be used in a reusable device platform, a limited use device platform, a re-posable use device platform, or a single-use/disposable device platform without departing from the scope of the disclosure. It will be appreciated that in a re-usable device platform an end-user is responsible for cleaning and sterilization of the device. In a limited use device platform the device can be used for some specified amount of times before becoming inoperable. Typical new device is delivered sterile with additional uses requiring the end-user to clean and sterilize before additional uses. In a re-posable use device platform a third-party may reprocess the device (e.g., cleans, packages and sterilizes) a single-use device for additional uses at a lower cost than a new unit. In a single-use/disposable device platform a device is provided sterile to the operating room and used only once before being disposed of.

Additionally, the teachings and principles of the disclosure may include any and all wavelengths of electromagnetic energy, including the visible and non-visible spectrums, such as infrared (IR), ultraviolet (UV), and X-ray.

It will be appreciated that various features disclosed herein provide significant advantages and advancements in the art. The following embodiments are exemplary of some of those features.

In the foregoing Detailed Description of the Disclosure, various features of the disclosure are grouped together in a single embodiment for the purpose of streamlining the disclosure. This method of disclosure is not to be interpreted as reflecting an intention that the claimed disclosure requires more features than are expressly recited in each claim. Rather, inventive aspects lie in less than all features of a single foregoing disclosed embodiment.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements.

Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

What is claimed is:

1. A digital imaging method for use with an endoscope in ambient light deficient environments comprising:
    actuating an emitter to emit a plurality of pulses of electromagnetic radiation to cause illumination within the light deficient environment;
    pulsing the emitter at a predetermined interval corresponding to a sensing interval of a pixel array; and
    sensing reflected electromagnetic radiation from a pulse with the pixel array to create an image frame in a plurality of cycles, each cycle including an integration period of the pixel array, wherein a duration of the integration period is variable from cycle to cycle in the plurality of cycles wherein said pixel array is actuated at a sensing interval that corresponds to the pulse interval of said emitter;
    stopping the emitter from pulsing for a single iteration;
    creating a dark frame by sensing the pixel array while the emitter is not pulsing a pulse;
    creating one or more reference frames, using said dark frame, for use in removing fixed pattern noise;
    removing fixed pattern noise from the image frame by subtracting stored reference data; and
    creating a stream of images by combining a plurality of image frames to form a video stream;
    wherein the method further comprises computing reference data for a particular integration duration by interpolating between two or more dark reference buffers established at two or more different integration times having two or more different duration lengths.

2. The method of claim 1,
    wherein one or more dark frames are created from one or more sensing of the pixel array while the emitter is not issuing electromagnetic energy, and
    wherein the one or more dark frames are created, interspersed within the image frames.

3. The method of claim 1, wherein said one or more reference frames are created upon startup of a system comprising a laser emitter and pixel array and stored within memory associated with the system.

4. The method of claim 3, wherein a plurality of reference frames may be established at different exposure times.

5. The method of claim 1, further comprising enhancing the precision of the one or more reference frames with continued sampling of subsequent single dark frames.

6. The method of claim 5, further comprising enhancing the precision of an existing reference frame by factoring in subsequent dark frame data, using exponential smoothing.

7. The method of claim 1, wherein each image frame is enhanced before being integrated into the video stream.

8. The method in claim 7, wherein the method further comprises subtracting data from a single dark reference buffer from an image frame.

9. The method of claim 1, wherein the method further comprises subtracting said reference data from an image frame.

10. The method of claim 1, wherein the emitter is a laser to emit a laser pulse of a wavelength of electromagnetic radiation to cause illumination within the light deficient environment.

11. The method of claim 1, wherein the emitter is an LED emitter to emit an LED pulse of a wavelength of electromagnetic radiation to cause illumination within the light deficient environment.

12. A system for digital imaging system for use in ambient light deficient environments comprising:
    one or more processors;
    one or more memory devices operably coupled to the one or more processors and storing executable and operational data, the executable and operational data effective to cause the one or more processors to:
        actuate a laser emitter to emit a plurality of pulses of electromagnetic radiation to cause illumination within the light deficient environment;
        pulse the laser emitter at a predetermined interval corresponding to a sensing interval of a pixel array;
        sense reflected electromagnetic radiation from the pulse with the pixel array to create an image frame in a plurality of cycles, wherein each cycle in the plurality of cycles includes an integration time of the pixel array, wherein a duration of the integration time is variable from cycle to cycle in the plurality of cycles, wherein said the pixel array is actuated at a sensing interval that corresponds to the pulse interval of said laser emitter;
        stop the emitter from pulsing for a single iteration;
        sense the pixel array while the emitter is not pulsing a pulse to create a dark frame;
        create one or more reference frames, using said dark frame, for use in removing fixed pattern noise;

remove fixed pattern noise from an image frame by subtracting values derived from one or more dark reference frames; and create a stream of images by combining a plurality of image frames to form a video stream;

wherein the executable and operational data is effective to cause the one or more processors to compute the reference data for a particular integration duration by interpolating between two or more dark reference buffers established at two or more different integration times having two or more different duration lengths.

13. The system of claim 12, wherein one or more dark frames are created from one or more sensing of the pixel array while the emitter is not issuing electromagnetic energy, and wherein the one or more dark frames are created, interspersed within the image frames.

14. The system of claim 12, wherein said one or more reference frames are created upon startup of a system comprising the laser emitter and pixel array and stored within memory associated with the system.

15. The system of claim 14, wherein a plurality of reference frames may be established at different exposure times.

16. The system of claim 12, wherein the executable and operational data is effective to cause the one or more processors to enhance the precision of the one or more reference frames with continued sampling of subsequent single dark frames.

17. The system of claim 16, wherein the executable and operational data effective to cause the one or more processors to enhance the precision of an existing reference frames by factoring in subsequent dark frame data, using exponential smoothing.

18. The system of claim 12, wherein each image frame is enhanced before being integrated into the video stream.

19. The system of claim 18, wherein the executable and operational data is effective to cause the one or more processors to subtract data from a single dark reference buffer from an image frame.

20. The system of claim 12, wherein the executable and operational data is effective to cause the one or more processors to subtract said reference data from an image frame.

* * * * *